United States Patent [19]

Grenci, deceased et al.

[11] 4,419,884
[45] Dec. 13, 1983

[54] TEST HEAD FOR COMPRESSED GAS CYLINDERS

[75] Inventors: Carl A. Grenci, deceased, late of Yorba Linda, Calif.; by William C. Jordan, executor, Laguna Hills, Calif.

[73] Assignee: La Nora J. Grenci, Yorba Linda, Calif.

[21] Appl. No.: 388,079

[22] Filed: Jun. 14, 1982

[51] Int. Cl.³ ............................................. G01M 3/02
[52] U.S. Cl. ........................................ 73/49.8; 73/37; 141/3
[58] Field of Search ...................... 73/49.8, 49.2, 45.4; 285/196; 374/208, 144

[56] References Cited

U.S. PATENT DOCUMENTS

| 2,581,536 | 1/1952 | Johns | 73/49.8 X |
| 3,058,760 | 10/1962 | Bankowski | 285/196 |
| 3,247,707 | 4/1966 | Tatro | 73/49.2 |
| 3,259,144 | 7/1966 | Taplin | 374/208 |
| 3,377,841 | 4/1968 | Neal | 73/49.7 X |
| 3,433,079 | 3/1969 | Wilson | 73/49.8 |
| 3,534,587 | 10/1970 | Grenci | 73/49.8 |

FOREIGN PATENT DOCUMENTS

2714408  3/1977  Fed. Rep. of Germany ........ 138/90

*Primary Examiner*—Daniel M. Yasich
*Attorney, Agent, or Firm*—Philip M. Hinderstein

[57] ABSTRACT

A test head useful in the testing of compressed gas cylinders capable of withstanding high pressure. The water jacket head includes a neck seal including a spud insertable into the neck of a compressed gas cylinder for permitting a high pressure seal to be made to the cylinder. The present neck seal incorporates a permanent quick-connect sleeve for which mating male spud insert units can be designed for nearly any size cylinder neck. Changing the spud insert can be accomplished by hand, without removing the head from its use location. A diaphragm support spring is installed between the moving spud stem assembly and the top plate of the head which biases the spud stem assembly, thus increasing diaphragm life and preventing increasing reassembly difficulty following spud changes. Studs and screws replace welds in holding the top, side and bottom plates together which greatly alleviates the task of servicing inside the head when leaks eventually occur in the moving elements. A heavy, long-lasting, fluid pressure expansible head boot is included which requires less servicing, simplifying field installation.

11 Claims, 5 Drawing Figures

TEST HEAD FOR COMPRESSED GAS CYLINDERS

BACKGROUND OF THE INVENTION

1. Field of the Invention

The present invention relates to a water jacket head and, more particularly, to a water jacket head useful in the testing of compressed gas cylinders and capable of withstanding high pressure.

2. Description of the Prior Art

High pressure steel cylinders conventionally are used to contain compressed gases for a wide variety of medical and industrial uses. Literally thousands of such compressed gas cylinders are in use daily to contain under pressure oxygen, nitrogen, hydrogen, argon and other gases. To minimize the possibility of rupture of such cylinders, with the associated dangers of explosion and/or loss of combustible or poisonous gas, periodic expansion testing to determine the plastic and elastic deformation of the cylinders normally is carried out.

In accordance with U.S. Interstate Commerce Commission regulations, compressed gas cylinders used in interstate commerce must be checked once every five years by subjecting the cylinder to an internal pressure one and two-thirds times the working or rated pressure of the cylinder. Conventionally, this testing is carried out hydrostatically by placing the cylinder in a water-filled jacket connected to a burette. High pressure water is introduced into the cylinder, the pressure being raised to the requisite one and two-thirds times the nominal pressure of the cylinder. Total expansion (plastic deformation) of the cylinder then is measured by noting on the burette the amount of water displaced from the jacket as a result of the cylinder expansion.

To measure permanent expansion (plastic deformation) and percentage permanent expansion, the internal cylinder pressure is released. If the cylinder returns to its original shape, the burette will return to its zero position. If the cylinder does not return to within 10% of its original shape, as indicated by the burette reading, the cylinder is considered defective. Such a cylinder could rupture when subjected subsequently to severe shock or stress while filled with high pressure compressed gas.

To carry out such hydrostatic testing of compressed gas cylinders, it is necessary to remove the normal gas valve from the cylinder and replace it with a sealing spud through which is introduced the high pressure test water. In the past, to prevent leakage of the high pressure water between the sealing spud and the neck of the cylinder, it was necessary to tighten the spud excessively. Typically, use of a four foot wrench or a power driven torquing machine was required to achieve a sufficiently leakproof metal-to-metal seal. The resultant joint between the hardened steel spud and cylinder neck often was so tight that it was difficult to remove the spud subsequent to the test. Moreover, such wrenching was excessively time consuming.

An alternative approach of the prior art to reduce torquing was to provide a thread sealing compound between the spud and the neck. This approach was disadvantageous because the compound had some tendency to extrude and leak under the high pressure, and more important, required time for application.

Still another approach of the prior art was to utilize an O-ring seal between the neck of the cylinder and the spud. While this approach reduced the torquing requirements, it suffered various other shortcomings. First, the top of the cylinder had to be very smooth, which was seldom the case with cylinders in daily use. As a result, it often was necessary to use a power grinder to smooth the cylinder neck prior to initiation of the test. This added an extra step to the test process and was hazardous, because the grinding had to be done at shoulder height, with the ever present danger that a spark could ignite residual flammable gas in the cylinder. Moreover, the cylinder neck surfaces tended to extrude or cut the O-rings, requiring constant O-ring replacement. Further, worn threads and the high pressures to which the O-rings were subjected tended to result in leaks through the seal, voiding the test.

A further problem encountered in the prior art was how conveniently to seal the water jacket lid or head. Often complicated lid structures having multiple clamps to hold them rigidly atop the jacket were required. Such arrangements were unsatisfactory in that often they permitted air and/or water leakage from the jacket. More important, such prior art water jacket head arrangements were time consuming to connect and disconnect. In facilities where many cylinders had to be tested, the operations of attaching and sealing the spud and sealing the lid on the test jacket consumed more time than the actual expansion test itself.

These and other shortcomings of the prior art are effectively solved by the hydrostatic test head and neck seal described and claimed in U.S. Pat. No. 3,534,587, issued Oct. 20, 1970, to Carl A. Grenci and entitled "Hydrostatic Neck Seal". The hydrostatic neck seal of the Grenci patent is adapted for incorporation in a water jacket test head. The patented device permits a high pressure neck seal to be made to a gas cylinder without the necessity for using torquing machines, sealing compounds or O-rings. The water jacket head itself includes a hydrostatic seal permitting the head to be connected to the jacket rapidly and without the use of mechanical clamps. The Grenci test head thus permits significant reduction in the time required to carry out hydrostatic testing of compressed gas cylinders.

The Grenci neck seal comprises a hydrostatic chamber, the lower surface of which comprises a circular metal plate. The upper surface of the chamber comprises an extensible diaphragm of rubber or the like, the central region of which is sandwiched between a pair of rigid discs of smaller diameter than the diaphragm. A thick walled cylindrical adapter is attached coaxially to the diaphragm and discs. An elongate tube having an outer diameter less than the inner diameter of the adapter is attached coaxially within the adapter and extends downwardly through a central hole in the chamber lower plate and through an axial opening in a sealing spud depending from the lower plate. The tube is thus free to move longitudinally in response to transverse displacement of the extensible diaphragm.

An expansible grommet surrounds a portion of the tube extending beyond the spud, one side of the grommet abutting against the lower threaded end of the spud. A nut or like annular fitting is fixedly attached to the tube, adjacent the other side of the grommet. With this arrangement, when water or other fluid is introduced into the hydrostatic chamber, the resultant longitudinal motion imparted to the tube by motion of the diaphragm forces the fitting to squeeze the grommet against the end of the spud, causing the grommet to expand radially. When the spud is threadingly inserted in the neck of a compressed gas cylinder, expansion of the grommet forms a high pressure seal in the cylinder neck.

Sealing water to operate the Grenci hydrostatic neck seal may be introduced into the hydrostatic chamber via the space between the inner wall of the cylindrical adapter and the outer wall of the tube extending within the cylinder. Appropriate fluid connections are provided to permit, e.g., high pressure water required for hydrostatic expansion testing to be introduced into a compressed gas cylinder via the seal.

The water jacket test head itself comprises an upper circular metal plate spaced by means of a metal cylinder from a lower annular metal plate, the hydrostatic neck seal being attached to the latter member. A continuous rubber sleeve surrounds the metal cylinder, attached thereto by a pair of punch-locked metal bands. By introducing water or like fluid into the space between the sleeve and cylinder, the sleeve is caused to expand, e.g., against the inner wall of a cylindrical water jacket, thereby providing a hydrostatic seal.

A water jacket test head incorporating the Grenci neck seal readily may be threadingly inserted in the neck of a standard compressed gas cylinder using hand force only. When the cylinder and head then are lowered into a water jacket, water provided to the neck seal hydrostatic chamber and the region between the rubber sleeve and cylinder wall accomplishes simultaneous sealing of the head to the water jacket and high pressure sealing of the cylinder neck. Control of this sealing water may be accomplished remotely from the water jacket, as at an appropriate control console.

While the hydrostatic neck seal of the Grenci patent represents a significant improvement in the state of the art, several problems have been encountered in the use thereof. Initially, one end of the spud must be screwed tightly by wrench into the spud plate on the head. The other end of the spud is then screwed by hand into the neck of the cylinder being tested, turning the entire head, which is in turn, attached to a hoist chain, in the process. Whenever the size of the neck of the cylinder being tested changes, the spud too has to be changed. This is, invariably, a time consuming process since the head has to be removed from the hoist, taken to a vise, and the spud removed with a wrench and subsequently replaced before reattaching to the hoist. Otherwise, spare heads containing different size spuds already assembled have to be maintained in stock (with attendant costs).

In the operation of the Grenci hydrostatic test head, the longitudinal motion imparted to the tube by motion of the diaphragm causes an increasing set in the upward position of the diaphragm, resulting in eventual diaphragm failure and leakage. The entire head is welded together, making the task of servicing inside the head difficult and time consuming. In the past, welds had to be broken or awkward fishing had to be done in attempting to make mechanical repairs through the spud plate hole. Finally, the continuous rubber sleeve which surrounds the metal cylinder does not last very long and replacement is time consuming and awkward as a result of the necessary head boot clamps.

SUMMARY OF THE INVENTION

To overcome these and other shortcomings of the Grenci hydrostatic test head, the present invention provides an improved neck seal also adapted for incorporation in a water jacket head. The present water jacket head includes all of the advantages of the Grenci head. In addition, however, the neck seal of the present water jacket head incorporates a permanent quick-connect sleeve for which mating male spud insert units can be designed for nearly any size cylinder neck. Changing the spud insert can be accomplished by hand, without removing the head from the hoist. This is simply done by removing the protector nut, jam nut, washers and grommet, pushing a coupling sleeve forward, and dropping out the spud insert. Replacing the spud reverses this process, which can be accomplished by hand at the same time. Thus, when the neck size of the cylinder being tested changes, the neck seal can be adapted thereto so that the spud screwed into the head does not have to be wrenched for removal and wrenched for insertion and additional heads with various size spuds do not have to be maintained in stock to prevent the time lost for spud changes in the head.

With the present water jacket head, a diaphragm support spring is installed between the moving spud stem assembly and the top plate which urges the diaphragm downwardly and prevents an increasing set in the upward position of the diaphragm, thus increasing diaphragm life and preventing increasing difficulty in affixing the protector nut, jam nut, washers and grommet to the spud stem after a spud change. Studs and screws replace welds in holding the top, side, and bottom plates together, which greatly alleviates the task of servicing inside the head when leaks eventually occur in the moving elements. Finally, the present test head incorporates a different type of fluid pressure expansible head boot which is heavier and lasts longer, consequently requiring less servicing, and no head boot clamps are needed, simplifying field installation.

Briefly, the neck seal of the present water jacket head comprises a hydrostatic or pneumatic chamber formed between a circular metal plate and an extensible diaphragm of rubber or the like, the central region of which is sandwiched between a pair of rigid discs of smaller diameter than the diaphragm. A thick-walled, cylindrical, pressurization adapter is attached coaxially to the diaphragm and discs. An elongate tube is attached coaxially to the adapter and extends downwardly through an axial opening in a removable sealing spud. The tube is free to move longitudinally in response to transverse displacement of the extensible diaphragm.

An expansible grommet or grommets surround a portion of the tube extending beyond the spud, one side of the grommet abutting against the lower threaded end of the spud. A jam nut or like annular fitting is fixedly attached to the tube, adjacent the other side of the grommet. With this arrangement, when air, water or other fluid is introduced into the chamber, the resultant longitudinal motion imparted to the tube by motion of the diaphragm forces the fitting to squeeze the grommet against the end of the spud, causing the grommet to expand radially. When the spud is threadingly inserted in the neck of a compressed gas cylinder, expansion of the grommet forms a high pressure seal in the cylinder neck. Sealing fluid to operate the neck seal may be introduced into the chamber by means of a channel through the cylindrical adapter. Appropriate fluid connections are provided to permit, e.g., high pressure water required for hydrostatic expansion testing to be introduced into a compressed gas cylinder via the seal.

A spud coupling supports a plurality of balls which engage the outer surfaces of the spud to prevent removal thereof. A movable coupling sleeve surrounding the spud coupling and the spud is biased in position to prevent retraction of the balls and removal of the spud. On the other hand, the coupling sleeve may be pushed forwardly to permit retraction of the balls and removal of the spud.

The water jacket head itself may comprise an upper circular metal plate spaced by means of a plurality of studs from a lower circular metal plate, the neck seal being attached to the lower plate. A novel head boot surrounds a side plate and extends between the upper and lower plates. By introducing air, water or like fluid into the space between the side plate and the boot, the boot is caused to expand, e.g., against the inner wall of a cylindrical water jacket, thereby providing a hydrostatic or pneumatic seal. Screws are used to connect the upper plate to the studs, making disassembly of the head much easier.

OBJECTS, FEATURES AND ADVANTAGES

It is therefore the object of the present invention to overcome the shortcomings encountered in use of the hydrostatic test head of U.S. Pat. No. 3,534,587. It is a feature of the present invention to overcome these shortcomings by incorporating into a neck seal a quick disconnect spud. An advantage to be derived is that the spud does not have to be wrenched for removal and wrenched for insertion. Another advantage is that additional heads with various size spuds do not have to be maintained in stock. Still another advantage is that changing of the spud insert can be accomplished by hand, without removing the head from the hoist.

A further feature of the present invention is a diaphragm support spring between the moving spud stem assembly and the top plate. An advantage to be derived is longer diaphragm life. A still further advantage is the prevention of increasing reassembly difficulty following spud changes.

A still further feature is the use of studs and screws to assemble the head. An advantage to be derived is a substantial simplification in making mechanical repairs.

Another feature is a newly designed head boot. An advantage is a head boot which lasts longer and requires less servicing. Still another advantage is the elimination of head boot clamps.

Still other objects, features, and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

DESCRIPTION OF THE PREFERRED EMBODIMENT

Figures 1, 3:
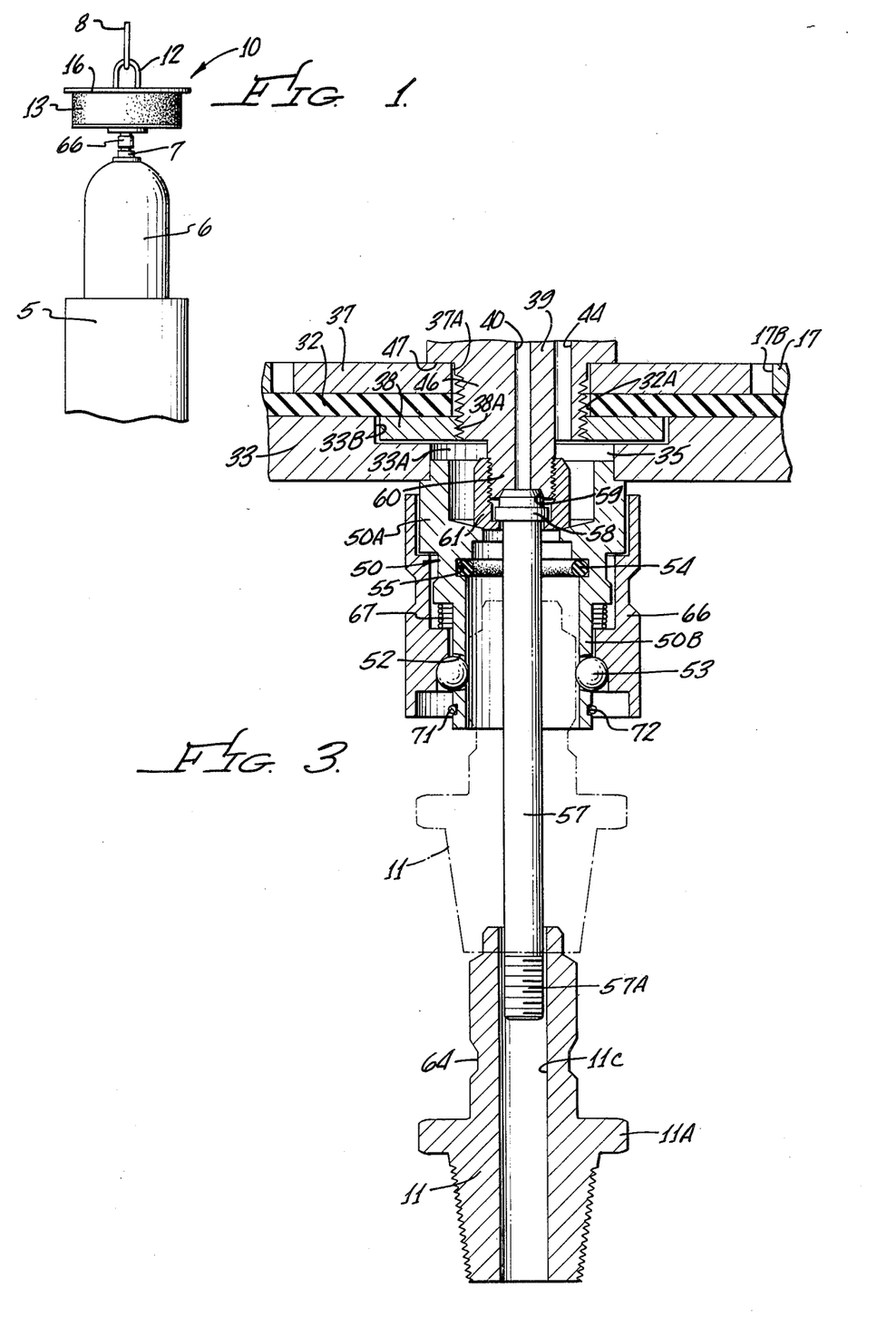
FIG. 1 is a front plan view of a portion of an apparatus for testing compressed gas cylinders, the apparatus including a water jacket and a water jacket head constructed in accordance with the teachings of the present invention.
FIG. 3 is an exploded longitudinal sectional view of portions of the neck seal of FIG. 2.

Since the present invention represents an improvement to the hydrostatic test head and neck seal of Grenci U.S. Pat. No. 3,534,587, reference should be had to such patent for a more complete description of an apparatus for hydrostatically testing compressed gas cylinders. For the purposes of the present invention, such test apparatus includes a water jacket 5, into which is placed a compressed gas cylinder 6 to be tested. A water jacket test head, generally designated 10, and constructed in accordance with the teachings of the present invention, provides a leakproof lid for jacket 5. As will be described hereinbelow, head 10 incorporates a neck seal by means of which high pressure fluid is prevented from escaping from cylinder 6. The test apparatus also comprises a console (not shown) housing a high pressure hydraulic or pneumatic pump (not shown) and various burettes, gauges and controls (not shown) useful for carrying out high pressure testing of cylinder 6.

As described more fully in the Grenci patent, jacket 5 is fabricated of steel or like material having sufficient strength so as not to be affected by expansion changes of cylinder 6 under test. Jacket 5 has an open upper end and a closed lower end. In a typical installation, jacket 5 may be mounted in a concrete well of sufficient depth so that a blow out disc (not shown) attached to jacket 5 is situated below the level of the floor. A water line (not shown) interconnects the interior of jacket 5 with a burette mounted on the control console.

Centrally extending from the underside of water jacket head 10 is a sealing spud 11 which threadingly engages the internally threaded neck 7 of compressed gas cylinder 6. Head 10 is provided with a lift eye 12 for engagement by the hook 8 of an appropriate overhead crane (not shown). This arrangement permits the crane to be used to insert and remove cylinder 6 from within water jacket 5. Head 10 is provided with a circumferential, expansible head boot 13 which is hydrostatically or pneumatically compressed against the inner surface of jacket 5 to effect an air and watertight seal therebetween.

High pressure fluid from the pump is supplied to a hose (not shown) which is adapted for attachment to a connector 14 on head 10. As will be described hereinbelow, connector 14 communicates via spud 11 with the interior of cylinder 6, thereby providing a conduit for introducing high pressure fluid into cylinder 6. The present seal incorporated in head 10 prevents leakage of this high pressure fluid into jacket 6. Sealing fluid, supplied from the console via a hose (not shown) adapted for attachment to a connector 15 on head 10, provides hydrostatic or pneumatic pressure both for the neck seal and for expansion of boot 13.

Details of head 10 may be best understood in conjunction with FIGS. 2, 3, 4 and 5. As shown therein, head 10 comprises an upper, disc-shaped, flat, steel plate 16, to the center of which is welded lift eye 12. Preferably, the diameter of upper plate 16 is equal to or greater than the outer diameter of water jacket 5. Connectors 14 and 15 are coupled to plate 16. Head 10 also comprises a lower, flat, steel plate 17 of annular shape, having an outer diameter slightly smaller than the inner diameter of water jacket 5. Lower plate 17 is attached in spaced, parallel relation with upper plate 16 by means of a plurality of spaced, parallel head studs 18. Each head stud 18 has a lower, reduced diameter section 18A which extends into a mating hole 17A in lower plate 17. A weld is made between section 18A and plate 17. The upper end of each head stud 18 has an internally threaded bore 18B and upper plate 16 has a series of holes 16B which are alignable with bores 18B. Screws 19 extend through holes 16B and are engageable with bores 18B to connect upper plate 16 to studs 18. By use of screws 19, upper plate 16 may be readily detached from lower plate 17, may greatly alleviates the task of servicing inside head 10 when leaks eventually occur in the moving elements.

Figure 2:
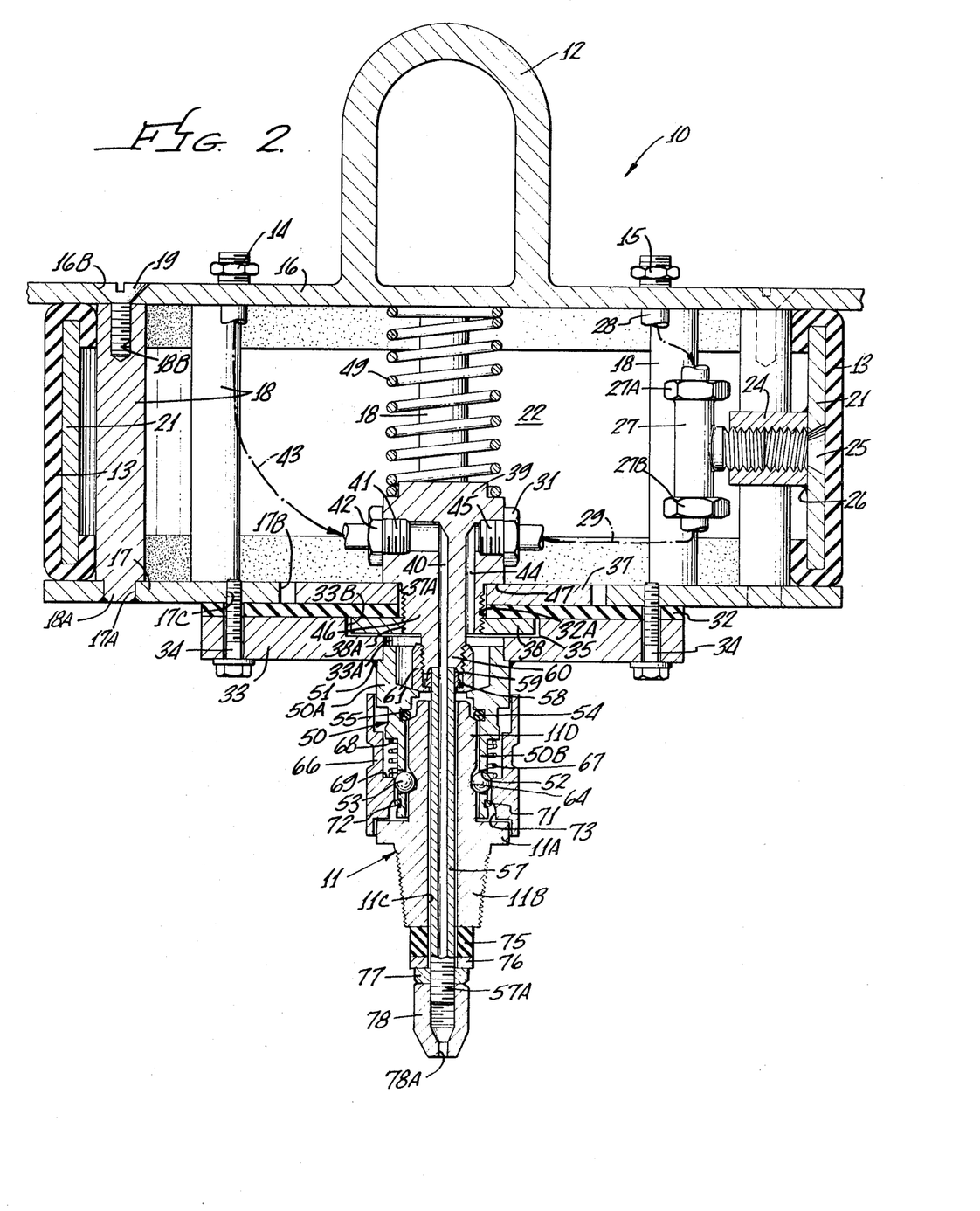
FIG. 2 is a longitudinal sectional view of the present water jacket head incorporating the present neck seal.

Head boot 13 is in the form of a sleeve of rubber or similar expansible material having a generally C-shaped cross section. Positioned within head boot 13 is a cylindrical side plate 21. Because of the flexibility of head boot 13, it is readily positioned around side plate 21. With head boot 13 surrounding side plate 21 and upper plate 16 removed from head studs 18, it is a simple matter to slide head boot 13 and side plate 21 down around head studs 18. Thereafter, upper plate 16 may be positioned as shown in FIG. 2 and connected to head studs 18 by means of screws 19. In this manner, upper plate 16, lower plate 17 and the combination of side plate 21 and head boot 13 form an interior chamber 22. It is also seen that the new construction of head boot 13 eliminates the necessity for circumferential steel bands and makes the replacement of head boot 13 a relatively simple matter.

Attached to the interior of side plate 21 is an internally threaded coupling or boss 24 which communicates, by means of a hole 25 in side plate 21, with the space between head boot 13 and side plate 21. Boss 24 may be welded to side plate 21, as shown at 26. A conventional male branch tee 27 threadingly engages coupling 24. As seen in FIG. 2, one end of a piece of tubing 28 may be attached between connector 15 and one branch 27A of tee 27. It will thus be appreciated that sealing fluid entrant through connector 15 will be directed via tubing 28 to the region between side plate 21 and boot 13 to thereby expand boot 13 outwardly to seal jacket 5, as explained more fully in the Grenci patent. Another length of tubing 29, coiled so as to provide flexibility, connects the other branch 27B of tee 27 to a coupling 31. As will be described in detail hereinbelow, tubing 29 and coupling 31 supply sealing fluid to the present neck seal.

Details of the present neck seal also are evident in FIGS. 2-5. As seen therein, a central opening 17B in lower plate 17 is covered by an extensible diaphragm 32 of rubber or like material. A disc-shaped, flat, metal spud plate 33 having a diameter substantially equal to that of diaphragm 32 and having a central opening 33A is maintained in contact with the opposite side of diaphragm 32 by means of a plurality of circumferentially spaced hex head cap screws 34 which extend through spud plate 33 and diaphragm 32, screws 34 threadingly engaging appropriately located threaded holes 17C in lower plate 17. Spud plate 33 also has an enlarged central opening 33B adjacent diaphragm 32. It will be appreciated that diaphragm 32 and spud plate 33 define a chamber 35 within hole 33B.

The middle of diaphragm 32 is sandwiched between a pair of metal rings 37 and 38. Ring 37 has an outside diameter which is less than that of opening 17B in lower plate 17; ring 38 preferably has an outside diameter which is somewhat smaller than that of hole 33B in plate 33. Rings 37 and 38 and diaphragm 32 are retained in sandwiched relationship by means of a pressurization adapter 39 comprising a thick-walled cylinder having a passageway 40 extending axially therethrough. Passageway 40 communicates with a threaded hole 41 in adapter 39 into which hole a coupling 42 extends. Coupling 42 is connected via a length of tubing 43 to connector 14 by means of which high pressure fluid may be supplied to the interior of cylinder 6, as will appear more fully hereinafter. Adapter 39 has another passageway 44 extending therethrough, parallel to passageway 40. Passageway 44 communicates with a threaded hole 45 into which hole coupling 31 is inserted. Passageway 44 also communicates with chamber 35 to permit sealing fluid to be connected to the present neck seal.

An externally threaded coaxial neck portion 46 of adapter 39 extends through axial openings 37A and 32A in ring 37 and diaphragm 32, respectively, and threadingly engages an axial, threaded opening 38A in ring 38. This arrangement fixedly seats a portion of ring 37 (adjacent opening 37A) against a shoulder 47 of adapter 39. This arrangement also permits unitary movement of adapter 39, rings 37 and 38, and a portion or diaphragm 32, transverse of lower plate 17, which elements are herein referred to as a moving spud stem assembly.

Depending from spud plate 33, coaxial with passageway 40 through adapter 39, is an elongate, cylindrical, sleeve-like spud coupling 50. The extreme upper end of spud coupling 50 extends into opening 33A in plate 33 and is welded thereto, as shown at 51. The upper portion 50A of spud coupling 50, which extends directly below spud plate 33, is hexagonal in its outer configuration, for reasons which will appear more fully hereinafter. The lower portion 50B of spud coupling 50 has a plurality of tapered holes 52 extending therearound, in each of which is positioned a ball 53. The diameter of balls 53 is smaller than the diameter of holes 52 at the external surface of section 50B of spud coupling 50, but larger than the diameter of holes 52 at the internal surface of section 50B of spud coupling 50. This insures that balls 53 can move radially outwardly but cannot pass radially inwardly through holes 52. An O-ring 54 is positioned within an internal groove 55 in spud coupling 50, for reasons which will appear more fully hereinafter.

One end of an elongate rigid tube 57 has a collar 58 brazed or otherwise connected thereto. Collar 58 extends into an axial bore 59 in an externally threaded axial head portion 60 of adapter 39. A nut 61 has a portion thereof surrounding tube 57 and threads for engaging the external threads of head portion 60. Tightening of nut 61 onto head portion 60 thereby connects the upper end of tube 57 to adapter 39. It is seen that the center of tube 47 is in fluid communication with passageway 40 in adapter 39.

Surrounding tube 57 is unitary sealing spud 11. The central portion 11A of spud 11 is preferably hex-shaped, for reasons which will appear more fully hereinafter. The lower portion 11B of spud 11 is appropriately threaded to engage the interior threads of cylinder 6 undergoing test. A passageway 11C extends axially through the entire length of spud 11, the diameter of passageway 11C being slightly greater than the outside diameter of tube 57. As will be apparent more fully hereinafter, a set of sealing spuds 11 may be provided having various size threaded portions 11B to accommodate cylinders having different internal neck diameters.

The upper portion 11D of sealing spud 11 has an external diameter which is just smaller than the internal diameter of lower portion 50B of spud coupling 50 so that spud portion 11D extends between tube 57 and spud coupling 50. Portion 11D of spud 11 has a circumferential groove 64 in the outer surface thereof adapted to receive balls 53. In the position shown in FIG. 2, balls 53 extend into groove 64, preventing axial movement of spud 11 relative to spud coupling 50. As will be described more fully hereinafter, radially outward movement of balls 53 out of groove 64 permits removal of spud 11 from tube 57. It should also be noted that in the position shown in FIG. 2, the upper end of portion 11D of spud 11 engages O-ring 54 to thereby provide a seal between portion 11D of spud 11 and spud coupling 50.

Surrounding lower portion 50B of spud coupling 50 and upper portion 11D of spud 11 is a coupling sleeve 66. The internal surfaces at both the upper and lower ends of sleeve 66 are hexagonal in shape, the upper end of sleeve 66 receiving upper portion 50A of spud coupling 50 and the lower end receiving central portion 11A of spud 11. In this manner, coupling sleeve 66 is prevented from rotating relative to the stationary spud coupling 50 and prevents the rotation of spud 11.

A spring 67 is positioned between a shoulder 68 on spud coupling 50 and a shoulder 69 on coupling sleeve 66. Spring 67 biases coupling sleeve 66 downwardly, as viewed in FIG. 2. A retaining ring 71 positioned within a circumferential groove 72 in the outer surface of portion 50B of spud coupling 50 prevents downward movement of coupling sleeve 66 beyond the position shown in FIG. 2. In this position, the inner diameter of coupling sleeve 66, directly below shoulder 69, is such as to retain balls 53 in their inwardmost position, extending into groove 64 in spud 11. As mentioned previously, in this position, spud 11 is prevented from axial movement.

Coupling sleeve 66 has an increased diameter tapered bore 73 at the lower end thereof. Coupling sleeve 66 is movable vertically upwardly, to the position shown in FIG. 3. Bore 73 is positioned such that it is aligned with balls 53 in the uppermost position of coupling sleeve 66. The diameter of bore 73 is such as to permit radially outward movement of balls 53 until the inner surfaces thereof are aligned with the inner surface of portion 50B of spud coupling 50. In this position, spud 11 is axially movable, as will be explained more fully hereinafter.

Tube 57 is of sufficient length so as to extend through the entire length of passageway 11C in spud 11 and to project somewhat beyond the bottom of portion 11B of spud 11. Tube 57 preferably is of stainless steel or the like, of sufficient wall thickness to withstand high pressure, and is externally threaded adjacent its projecting end 57A. An expansible grommet or grommets 75 is/are disposed about the projecting end 57A of tube 57. Grommet 75 preferably is of rubber or like material and of sufficient length so as to insure radial expansion when compressed longitudinally. The inner diameter of grommet 75 is appropriate to insure a slidable fit about the outer perimeter of tube 57. Expansible grommet 75 is retained in place by a washer 76 and a jam nut 77 which threadingly engages the lower end 57A of tube 57. Damage to end 57A, which could occur if the device were carelessly inserted into cylinder 6, is prevented by an acorn nut 78 which threadingly engages end 57A of tube 57. Acorn nut 78 includes an orifice 78A permitting communication between tube 57 and the interior of cylinder 6. It will be appreciated that high pressure fluid supplied to connector 14 will flow through tubing 43, coupling 42, hole 42, passageway 40, tube 57 orifice 78A of acorn nut 78 into cylinder 6.

A diaphragm support spring 49 extends between adapter 39 of the spud stem assembly and plate 16 so a to axially bias adapter 39 downwardly, as viewed in FIG. 2, and to maintain diaphragm 32 in contact with spud plate 33. Spring 49 returns the spud stem assembly to its downward position following a test, preventing an increasing set in the upward position of diaphragm 32, thus increasing the life of diaphragm 32 and preventing increasing difficulty in affixing protector nut 78, jam nut 77, washer 76 and grommet 75 to end 57A of tube 57 after a change of spud 11.

The operation of head 10 as a water jacket seal and as a neck seal is similar to the operation of the head and neck seal of the Grenci patent. Adapter 39, ring 37, diaphragm 32 and ring 38, forming the spud stem assembly, are adapted for limited axial motion with respect to lower plate 33. Should adapter 39 move upwardly (toward upper plate 16), tube 57 likewise will move upwardly, pulling with it washer 76 and nuts 77 and 78. This in turn will force washer 76 against the lower end of expansible grommet 75, causing grommet 75 to expand outwardly, firmly engaging the interior wall of the neck of cylinder 6 under test. Grommet 75 thus seals neck 7, preventing leakage therethrough of fluid contained within cylinder 6.

The force for moving the spud stem assembly upwardly within interior chamber 22 is provided hydrostatically or pneumatically by means of the sealing water or other fluid entrant into water jacket head 10 by means of connector 15. This sealing fluid communicates via tubing 28 and 29 into chamber 35. Some of this fluid will also be present within opening 33A in spud plate 33 and the interior region of portion 50A of spud coupling 50. However, this fluid will be prevented from leaking out of spud coupling 50 by O-ring 55 and the sealing effect of grommet 75.

As the pressure of the sealing fluid is increased, considerable pressure will be exerted within chamber 35 on extensible diaphragm 32, displacing diaphragm 32, rings 37 and 38 and adapter 39 upwardly toward upper plate 16. As described, this upward motion of the spud stem assembly will cause outward expansion of sealing grommet 75 into firm sealing contact with the interior wall of neck 7 of cylinder 6. In a typical embodiment, the area of diaphragm 32 exposed within chamber 35 is such that sealing fluid under pressure of approximately 50 p.s.i. will exert a force against diaphragm 32 of about 900 pounds. This is more than sufficient to provide, by means of expansible grommet 75, a neck seal capable of withstanding very high pressures within cylinder 6.

It will also be noted that the sealing pressure applied to chamber 35 also passes via tee 27 into the space between boot 13 and side plate 21. This pressure causes expansion of boot 13, to seal the upper end of water jacket 5. For a more detailed explanation of the operation of compressed gas cylinder testing apparatus incorporating head 10, reference should be made to the beforementioned Grenci patent.

Figures 4, 5:
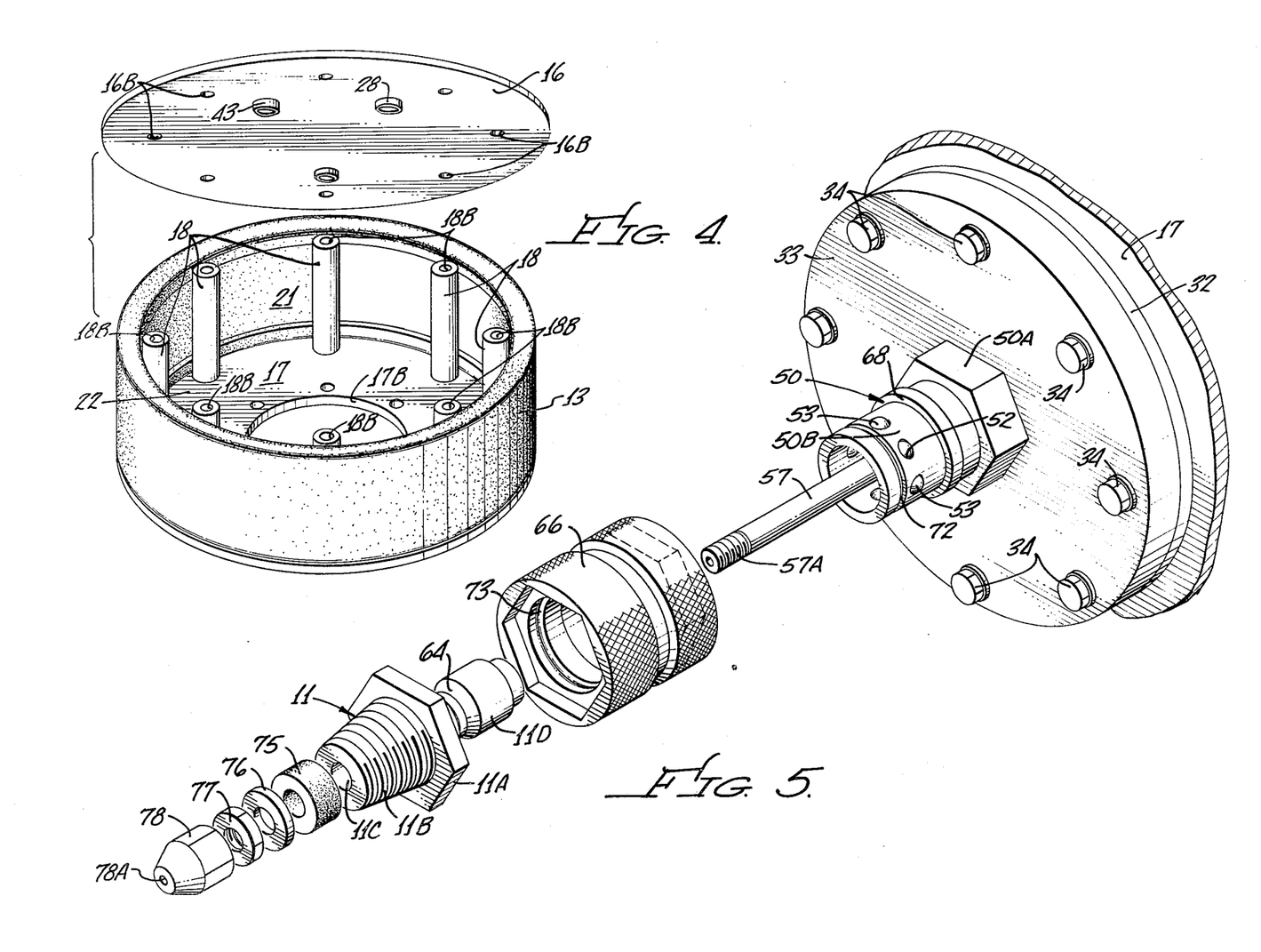
FIG. 4 is an exploded perspective view of portions of the water jacket head of FIG. 2.
FIG. 5 is an exploded perspective view of portions of the neck seal of FIG. 2 showing the details of the quick-disconnect spud.

The operation of the quick disconnect spud feature of the present invention can be understood with reference to FIGS. 2, 3 and 5. FIG. 2 shows the normal position of coupling sleeve 66 in which balls 53 are held in groove 64 in spud 11. With the construction of the Grenci patent, changing of the spud was a time consuming process, since the head had to be removed from the hoist, taken to a vise, and the spud removed and replaced with a wrench before reattaching to the hoist. According to the present invention, changing of spud 11 can be accomplished by hand without removing head 10 from the hoist. This is done by removing acorn nut 78, nut 77, washer 76 and grommet(s) 75. If, at this time, coupling sleeve 66 is pushed forwardly to the position shown in FIG. 3, compressing spring 67, spud 11 will immediately drop out of spud coupling 50. This is because the tapered surface of groove 64 urges balls 53 outwardly into bore 73 in coupling sleeve 66, as shown in FIG. 3.

Placing a new spud 11 into head 10 proceeds in the same manner. As a new spud 11 is removed from the position shown in solid lines in FIG. 3 to the position shown in phantom, the tapered leading outer surface of upper portion 11D of spud 11 forces balls 53 outwardly so that spud 11 can be moved to the position shown in solid lines in FIG. 2. Once in this position, sleeve 66 is released, whereupon spring 67 returns sleeve 66 to the position shown in FIG. 2 where balls 53 are held in groove 64 in spud 11. During the use of spud 11, the engagement of hexagonal portion 11A of spud 11 and the hexagonal recess in the lower end of sleeve 66 and the similar interconnection between portion 50A of spud if spud coupling 50 and the hexagonal recess in the upper end of coupling sleeve 66 prevents rotation of either sleeve 66 or spud 11.

While the invention has been described with respect to the preferred physical embodiment constructed in accordance therewith, it will be apparent to those skilled in the art that various modifications and improvements may be made without departing from the scope and spirit of the invention. Accordingly, to is to be understood that the invention is not to be limited by the specific illustrative embodiment, but only by the scope of the appended claims.

I claim:

1. In a test head for sealing the threaded neck of a compressed gas cylinder or the like of the type comprising a rigid support member, a spud adapted for threaded engagement with said neck, said spud having an axial opening extending therethrough, means defining a chamber in said test head, said means comprising a movable diaphragm, the perimeter of which is connected to said support member, and a hollow, cylindrical coupling member rigidly connected to said support member, an elongate member extending through said axial opening in sid spud, means for connecting one end of said elongate member to said diaphragm, an expansible grommet surrounding the other end of said elongate member, and a fitting fixedly attached to said other end of said elongate member, said grommet being positioned between said spud and said fitting whereby longitudinal motion of said elongate member imparted by movement of said diaphragm causes said grommet to be compressed between said fitting and said spud, the improvement comprising quick-disconnect means for said speed comprising:
 a coupling sleeve surrounding said coupling member and mounted for movement between first and second positions; and
 means operatively associated with said coupling sleeve for locking said spud in a desired axial position relative to said elongate member in said first position of said coupling sleeve and for permitting slidable movement of said spud relative to said elongate member in said second position of said coupling sleeve whereby said spud may be detached from said test head upon movement of said coupling sleeve from said first to said second position.

2. In test head according to claim 1, the improvement wherein said locking means comprises:
 a circumferential groove in the outer surface of said spud; and
 means for engaging said groove in said spud for preventing slidable movement of said spud relative to said elongate member.

3. In a test head according to claim 2, the improvement wherein said locking means further comprises:
 a plurality of holes extending through said coupling member, spaced therearound, and wherein said engaging means comprises:
 a plurality of balls mounted within said holes in said coupling member.

4. In a test head according to claim 3, the improvement wherein said coupling sleeve is mounted for axial movement between said first and second positions, said coupling sleeve having a first section having a first inside diameter alignable with said balls in said first position thereof and a second section having a second, larger inside diameter alignable with said balls in said second position thereof, said first section engaging said balls and maintaining said balls in said groove in said spud, said second section permitting radially outward movement of said balls out of said groove in said spud.

5. In a test head according to claim 4, the improvement wherein said locking means further comprises:
 means for biasing said coupling sleeve in said first position thereof.

6. In a test head useful in the testing of compressed gas cylinders or the like of the type comprising an upper circular plate, a lower annular plate, means for connecting said upper plate to said lower plate in parallel, spaced relationship thereto, a continuous expansible sleeve surrounding said connecting means and extending between said upper and lower plates, a spud adapted for threaded engagement with the neck of said cylinder, said spud having an axial opening extending therethrough, means defining a chamber in said test head, said means comprising a movable diaphragm, the perimeter of which is connected to said lower plate, and a hollow, cylindrical coupling member connected to said lower plate, said sput being attached to said coupling member, an elongate member extending through said axial opening in said spud, means for connecting one end of said elongate member to said diaphragm, an expansible grommet surrounding the other end of said elongate member, and a fitting fixedly attached to said other end of said elongate member, said grommet being positioned betweeen said spud and said fitting whereby longitudinal motion of said elongate member in a first direction imparted by movement of said diaphragm causes said grommet to be compressed between said fitting and said spud, the improvement comprising:
 a spring positioned between said upper metal plate and said connecting means for biasing said elongate member in a direction opposite to said first direction to prevent a set in said diaphragm.

7. In a test head useful in the testing of compressed gas cylinders or the like of the type comprising an upper circular plate, a lower annular plate, means for connecting said upper plate to said lower plate in parallel, spaced relationship thereto, a continuous expansible sleeve surrounding said connecting means and extending between said upper and lower plates, a spud adapted for threaded engagement with the neck of said cylinder, said spud having an axial opening extending therethrough, means defining a chamber in said test head, said means comprising a movable diaphragm, the perimeter of which is connected to said lower plate, and a hollow, cylindrical coupling member connected to said lower plate, said spud being attached to said coupling member, an elongate member extending through said axial opening in said spud, means for connecting one end of said elongate member to said diaphragm, an expansible grommet surrounding the other end of said elongate member, and a fitting fixedly attached to said elongate member, said grommet being positioned between said spud and said fitting whereby movement of said diaphragm causes said grommet to be compressed between said fitting and said spud, the improvement wherein said means for connecting said upper plate to said lower plate comprises:

a plurality of spaced, parallel studs, first ends of said studs being connected to said lower plate; and     means for releasably connecting said upper plate to the other ends of said studs; and further comprising:

a cylindrical side plate, said expansible sleeve having a generally C-shaped cross section and being positioned around said side plate with the opening in said sleeve facing inwardly, said sleeve and said side plate surrounding said studs and extending between said upper and lower plates.

8. In a test head according to claim 7, the improvement wherein said other end of each of said studs has an internally threaded bore, wherein said upper plate has a series of holes which are alignable with said bores in said studs, and wherein said means for releasably connecting said upper plate to said studs comprises:

a plurality of screws extendible through said holes in said upper plate and into said bores in said studs.

9. In a test head according to claim 7, the improvement further comprising:

means for conducting fluid pressure through said side plate and into the space between said side plate and said expansible sleeve.

10. In a test head useful in the testing of compressed gas cylinders or the like of the type comprising an upper circular plate, a lower annular plate, means for connecting said upper plate to said lower plate in parallel, spaced relationship thereto, a continuous expansible sleeve surrounding said connecting means and extending between said upper and lower plates, a spud adapted for threaded engagement with the neck of said cylinder, said spud having an axial opening extending therethrough, means defining a chamber in said test head, said means comprising a movable diaphragm, the perimeter of which is connected to said lower plate, and a hollow, cylindrical coupling member connected to said lower plate, said spud being attached to said coupling member, an elongate member extending through said axial opening in said spud, means for connecting one end of said elongate member to said diaphragm, an expansible grommet surrounding the other end of said elongate member, and a fitting fixedly attached to said elongate member, said grommet being positioned between said spud and said fitting whereby movement of said diaphragm causes said grommet to be compressed between said fitting and said spud, the improvement comprising:

a cylindrical side plate, the height of said side plate being less than the spacing between said upper and lower plates, and wherein:

said expansible sleeve has a generally C-shaped cross section and is positioned around said side plate, with the opening in said sleeve facing inwardly, said sleeve and said side plate surrounding said plates connecting means and extending between said upper and lower plates.

11. In a test head according to claim 10, the improvement further comprising:

means for conducting fluid pressure through said side plate and into the space between said side plate and said expansible sleeve.

\* \* \* \* \*